(12) United States Patent
Hashizume et al.

(10) Patent No.: US 9,480,450 B2
(45) Date of Patent: Nov. 1, 2016

(54) SCATTER COMPONENT ESTIMATING METHOD

(71) Applicant: SHIMADZU CORPORATION, Kyoto-shi, Kyoto (JP)

(72) Inventors: Nobuya Hashizume, Kyoto (JP); Keishi Kitamura, Kyoto (JP); Yoshiyuki Yamakawa, Kyoto (JP); Tetsuya Kobayashi, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 0 days.

(21) Appl. No.: 14/523,776

(22) Filed: Oct. 24, 2014

(65) Prior Publication Data

US 2015/0146952 A1    May 28, 2015

(30) Foreign Application Priority Data

Nov. 27, 2013  (JP) .................. 2013-245375

(51) Int. Cl.
  *G06K 9/00* (2006.01)
  *A61B 6/00* (2006.01)
  *A61B 6/03* (2006.01)
  *G06T 11/00* (2006.01)

(52) U.S. Cl.
  CPC ............. *A61B 6/5235* (2013.01); *A61B 6/037* (2013.01); *A61B 6/4208* (2013.01); *A61B 6/483* (2013.01); *A61B 6/502* (2013.01); *A61B 6/5205* (2013.01); *G06T 11/005* (2013.01)

(58) Field of Classification Search
  USPC ...................................................... 382/131
  See application file for complete search history.

(56) References Cited

U.S. PATENT DOCUMENTS

| | | | | |
|---|---|---|---|---|
| 6,408,049 B1* | 6/2002 | Edic et al. | ................ | 378/98.12 |
| 7,519,143 B2* | 4/2009 | Debasish et al. | ................. | 378/7 |
| 2009/0290682 A1* | 11/2009 | Star-Lack et al. | ............. | 378/87 |
| 2011/0103543 A1* | 5/2011 | Flohr | ................................ | 378/4 |

OTHER PUBLICATIONS

Bailey et al., "A convolution-subtraction scatter correction method for 3D PET", Phys. Med. Biol. 39 (1994), pp. 411-424.

* cited by examiner

*Primary Examiner* — Yon Couso
(74) *Attorney, Agent, or Firm* — McDermott Will & Emery LLP (57) ABSTRACT

In a reconstruction processing (S1), reconstruction processing is performed to list mode data to firstly capture a reconstruction image. Then, in a projection step (S2), the reconstruction image obtained in the reconstruction processing step is projected to capture a projection image. In a scatter component extracting step S4, low-frequency components are extracted from the projection image obtained in the projection step to obtain scatter components. Even when the data contains a missing region, the reconstruction processing unlikely to be influenced by the missing region suppresses the influence by the missing, and the resultant reconstruction image is projected. Consequently, the projection image having dummy data being interpolated to the missing region is obtainable. As a result, projection from the list mode data through the reconstruction image achieves the projection image with no missing data. Accordingly, precious estimation of the scatter components is obtainable.

12 Claims, 8 Drawing Sheets

EMISSION RECONSTRUCTION IMAGE

EMISSION FP IMAGE

SCALED SCATTER FP IMAGE

EMISSION SINOGRAM

SCATTER COMPONENT ESTIMATING METHOD

CROSS-REFERENCE TO RELATED APPLICATIONS

This application claims priority to Japanese Patent Application No. 2013-245375 filed Nov. 28, 2013 the subject matter of which is incorporated herein by reference in entirety.

TECHNICAL FIELD

The present invention relates to a scatter component estimating method for estimating scatter components of radiation from data collected in a radiation tomography apparatus.

BACKGROUND ART

Examples of an emission tomography apparatus include a PET (Positron Emission Tomography) apparatus. The PET apparatus reconstructs a tomographic image of a subject only when a plurality of detectors detects radiation (γ-rays) coincidentally generated due to annihilation of positive electrons (positrons) (i.e., only when radiation is counted coincidentally). In particular, the PET apparatus is also referred to as a "positron tomography apparatus".

Figure 10A:
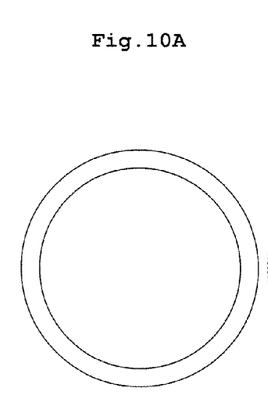
FIG. 10A is a schematic front view of a full-ring detector unit.
Figure 10B:
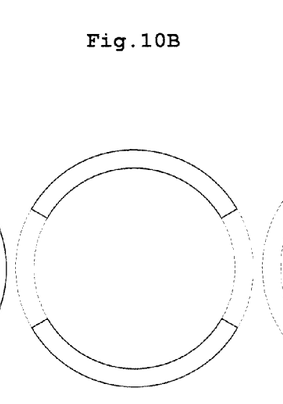
FIG. 10B is a schematic front view of a partial-ring detector unit other than a C-shape one.
Figure 10C:
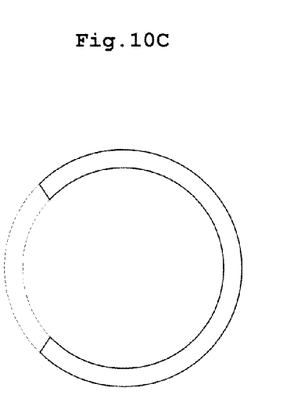
FIG. 10C is a schematic front view of a C-shape detector unit.

Examples of a PET apparatus include one as illustrated in FIG. 10A with a so-called "full-ring" type detector unit. The detector unit has various detectors arranged in a ring shape. The examples of a PET apparatus also include one as illustrated in FIG. 10B with a detector unit a part of which is open. The detector unit is so-called a "partial-ring" and a part thereof is missing. Examples of a PET apparatus with the "partial-ring" detector unit include a mammography PET apparatus configured to capture a reconstructed image of the breast. The mammography PET apparatus has a C-shape detector unit as the partial-ring detector unit as illustrated in FIG. 10C. The PET apparatus with various detectors not being arranged in a ring shape and thus having a blank area allows the detector unit to approach a subject flexibly depending on a size of the subject, thereby achieving flexible tomography. Such the apparatus is not limited to one illustrated in FIG. 10B or FIG. 10C.

Here, data of the γ-rays from the subject with radiopharmaceutical administered thereto is referred to as "emission data". Data obtained for absorption correction by externally emitting radiation of the same type as radiopharmaceutical is referred to as "transmission data". Examples of a projection image of the emission data include a sinogram. The sinogram has a longitudinal axis in an angle direction and a horizontal axis in a uniaxial direction of an orthogonal coordinate system (e.g., an x-coordinate in arrangement of detectors). Reconstruction processing is performed to the sinogram to capture a reconstruction image.

In recent years, a reconstruction method is mainly used for capturing a reconstruction image by performing reconstruction processing to data referred to as "list mode" (referred to as "list mode data" or "list data"). The data is detection event information of γ-rays (e.g., a detector number, a detection time, and energy of γ-rays) stored in time sequence. Such the reconstruction method is called "list mode reconstruction".

The data collected in the radiation tomography apparatus contains scatter components of radiation. Then, an estimating technique of estimating the scatter components of radiation has been suggested. See, for example, Non-Patent Literature 1. The technique in the Non-Patent Literature 1 is called a "convolution-subtraction method". In the method, superimposition integration is performed to projection data of the emission data for estimating the scatter components under the concept that the scatter components in the emission data have distribution with broad spread (space distribution with low-frequency components). The data used in the Non-Patent Literature 1 is obtained with a PET apparatus having a full-ring detector unit.

Non-Patent Literature 1: Dale L Bailey, "A Convolution-subtraction scatter correction method for 3D PET", Phys. Med, Boil. 39 (1994) 411-424)

SUMMARY OF INVENTION

Technical Problem

The mammography PET apparatus with the detector unit having various detectors arranged in a C-shape generates a missing region in the sinogram due to the blank area of the detectors. Accordingly, the scatter components cannot be estimated preciously from the defective sinogram with the missing data using the method of the Non-Patent Literature 1 mentioned above. Then, it is conceivable to use a method of estimating the scatter components after estimating the missing data for interpolating the sinogram. However, a false image (artifact) occurs around the missing data derived from the missing data. Consequently, it is impossible to estimate the missing data preciously.

The present invention has been made regarding the state of the art noted above, and its object is to provide a scatter component estimating method that allows precious estimation of scatter components.

Solution to Problem

The above object is fulfilled, according to this invention, by a scatter component estimating method for estimating scatter components of radiation from data collected in a radiation tomography apparatus. The method includes a reconstruction processing step of performing reconstruction processing to event data obtained by detecting the radiation to capture a reconstruction image, a projecting step of projecting the reconstruction image obtained in the reconstruction processing to capture a projection image, and a scatter component extracting step of extracting low-frequency components from the projection image obtained in the projecting step to obtain scatter components.

Operation and Effect

In a currently-used method, reconstruction processing is performed to histogram or list mode data to finally obtain a reconstruction image. Moreover, in the Non-Patent Literature 1, the scatter components are directly estimated from the sinogram. In contrast to this, the scatter component estimating method according to one embodiment of the present invention differs from the above methods. Specifically, in the reconstruction processing step, the reconstruction processing is performed to the event data to capture a reconstruction image firstly. Then, in the projecting step, the reconstruction image obtained in the reconstruction processing is projected to capture the projection image. Thereafter, in the scatter component extracting method, the low-frequency components are extracted from the projection image obtained in the projecting step to obtain the scatter components. In this manner, the reconstruction image obtained from the event data is not used as final data. The low-frequency components are extracted from the projection image obtained from the event data through the reconstruction image for obtaining the scatter components. In other words, in order to apply the method of the Non-Patent Literature 1 to the sinogram containing the data with the missing region, the missing region has to be removed. Accordingly, even when the data contains the missing region, reconstruction processing unlikely to be influenced by the missing is performed to the data. Consequently, the influence from the missing can be suppressed. Moreover, the reconstruction image is projected, whereby a projection image is obtainable having dummy interpolated data in the missing region. As a result, projecting from the event data through the reconstruction image achieves a projection image with a suppressed influence from the missing data. Then, precious estimation of the scatter components is obtainable by extracting the low-frequency components from the projection image.

It is preferable that the scatter component estimating method according to the embodiment of the present invention mentioned above includes a scatter component scaling step of performing scaling of the scatter components obtained in the scatter component extracting step using the projection image and contour information of the subject. An error occurs in distribution between the projection image of the estimated scatter components and the projection image of the emission data. Then, the error is reduced by scaling the projection image of the estimated scatter components such that the distribution thereof conforms to that of the projection image of the emission data. At this time, the scaling can be performed using the contour information of a subject.

The contour information of the subject may be form information such as the transmission data mentioned above, or CT data obtained with an X-ray CT apparatus. Alternatively, the form information may be obtained from the projection image of the emission data through contour extraction. Assuming that the projection image is a sinogram composed of an angle direction and a uniaxial direction of an orthogonal coordinate system, a one-dimensional addition profile in the uniaxial direction is determined with count values of the radiation being added in the angle direction of the sinogram. Then, a ratio in one-dimensional addition profile of the projection image to the scatter components obtained in the scatter component extracting step is determined from lateral distribution of the contour information of the subject mentioned above. Thereafter, a scaling coefficient is determined in accordance with the ratio in the one-dimensional addition profile for using the scaling coefficient in scaling the scatter components.

In the scatter component estimating method according to the embodiment of the present invention mentioned above, one example of the reconstruction processing in the reconstruction processing step is an iterative approximation method by which an image is iteratively approximated with the event data.

The scatter component estimating method of the present invention mentioned above is especially advantageous for using the data as the data with the missing region. That is, the radiation tomography apparatus includes a detector unit a part of which is open. The scatter component estimating method according to the embodiment of the present invention is advantageous for estimating the scatter components of the radiation using data with a missing region from the event data. The data with the missing region is obtained with the detector unit and is thus partially missing. As mentioned above, the reconstruction unlikely to be influenced from the missing is performed to reduce an influence of the missing. Accordingly, dummy data is interpolated to the missing region of the projection image obtained by projecting the reconstruction image. Then, the resultant is used as the projection image with a suppressed influence of the missing data. Consequently, precious estimation of the scatter components is obtainable by extracting the low-frequency components from the projection image. Of course, the above is applicable for use of the data obtained with the full-ring detector unit illustrated in FIG. 10A.

The scatter component estimating method according to the embodiment of the mentioned above includes a slice expanding step of expanding a slice of the projection image obtained from the event data. In the scatter component extracting step, the low-frequency components are extracted from the projection image having been expanded in the slice expanding step for obtaining the scatter components. Such is preferable. When radioactivity distribution exists outside the field of view, the slice is expanded by increasing the number of slices of the projection image under consideration of the radioactivity distribution. When the slice of the projection image fails to be expanded with the radioactivity distribution outside the field of view, the scatter components are underestimated at the end of the subject (e.g., in the vicinity of the root of the breast close to the trunk when a photographing object is the breast). Thereafter, the scatter components are scaled extremely to be overestimated. The slice of the projection image is expanded with the radioactivity distribution outside the field of view, leading to elimination of the underestimation of the scatter components at the end. Accordingly, overestimating the scatter components can be prevented without the following extreme scaling of the scatter components.

Advantageous Effects of Invention

With the scatter component estimating method according to the embodiment of the present invention, the reconstruction processing is performed to the event data in the reconstruction processing step to capture the reconstruction image firstly. Then, in the projecting step, the reconstruction image obtained in the reconstruction processing step is projected to capture the projection image. In the scatter component extracting step, the low-frequency components are extracted from the projection image obtained in the projecting step to obtain the scatter components. As noted above, even when the data contains the missing region, the reconstruction processing unlikely to be influenced by the missing region suppresses the influence by the missing, and the resultant reconstruction image is projected. Consequently, the projection image having dummy data being interpolated to the missing region is obtainable. As a result, projection from the event data through the reconstruction image achieves the projection image with a suppressed influence by the missing data. Accordingly, precious estimation of the scatter components is obtainable by extracting the low-frequency components from the projection image.

It is to be understood that both the foregoing general description and the following detailed description are exemplary and explanatory and are intended to provide further explanation of the invention as claimed.

BRIEF DESCRIPTION OF DRAWINGS

The accompanying drawings, which are included to provide a further understanding of the invention and are incorporated in and constitute a part of this specification, illustrate embodiments of the invention, and together with the description Serve to explain the principles of the invention.

For the purpose of illustrating the invention, there are shown in the drawings several forms which are presently preferred, it being understood, however, that the invention is not limited to the precise arrangement and instrumentalities shown.

DESCRIPTION OF EMBODIMENTS

The invention is described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure is thorough, and will fully convey the scope of the invention to those skilled in the art. In the drawings, the size and relative sizes of layers and regions may be exaggerated for clarity. Like reference numerals in the drawings denote like elements.

Embodiment

Figure 1:
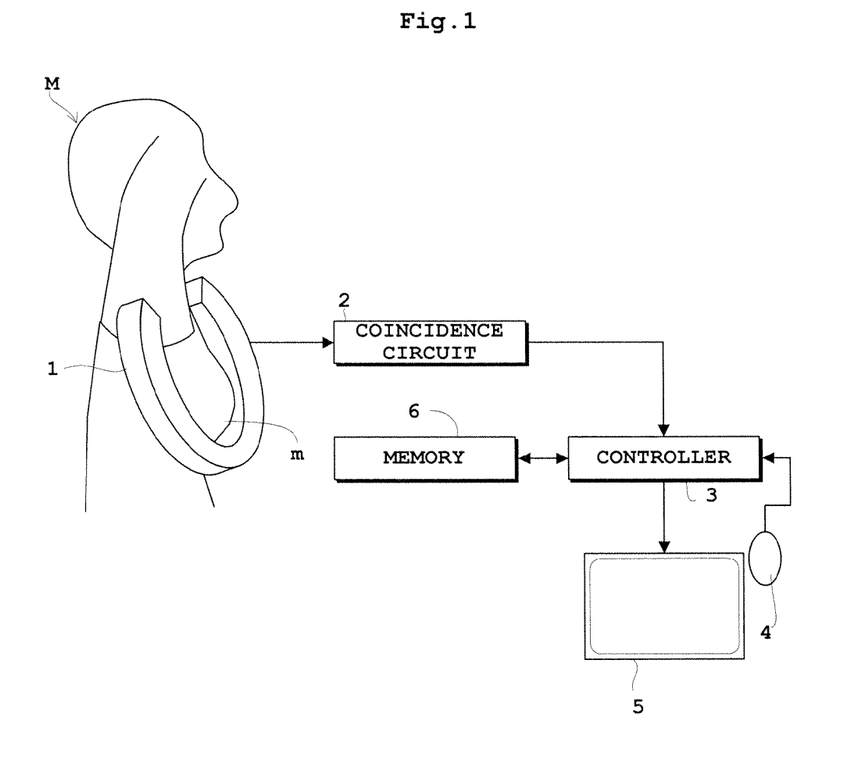
FIG. 1 is a side view and a block diagram of a PET (Positron Emission Tomography) apparatus according to one embodiment of the present invention.
Figure 2:
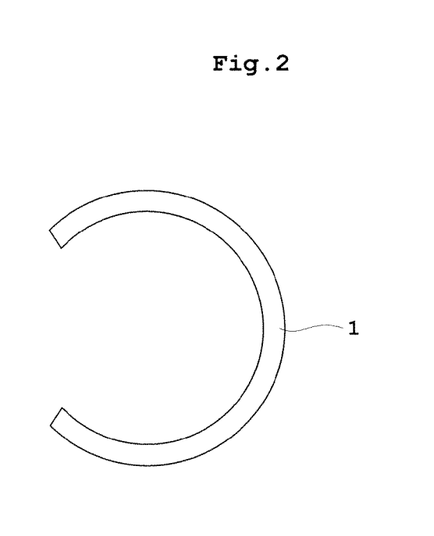
FIG. 2 is a schematic front view of a detector unit.

The following describes embodiments of the present invention with reference to drawings. FIG. 1 is a side view and a block diagram of a PET (Positron Emission Tomography) apparatus according to one embodiment. FIG. 2 is a schematic front view of a detector unit. The embodiment describes a mammography PET apparatus as one example of an emission tomography apparatus. Moreover, the embodiment describes a C-shape detector unit illustrated in FIG. 2 (see also FIG. 10C) as one example of a detector unit a part of which is open.

As illustrated in FIG. 1, the PET apparatus according to the embodiment includes a C-shape detector unit 1 surrounding the breast m of a subject M. In the embodiment, various γ-ray detectors (not shown) are arranged to form the C-shape detector unit 1 a part of which is open as illustrated in FIG. 2. The detector unit 1 corresponds to the detector unit in the embodiment.

In the embodiment, the C-shape detector unit 1 is formed by twelve γ-ray detectors measuring 50 mm per side. Moreover, the C-shape detector unit 1 having a blank area for two detectors is formed by arranging twelve γ-ray detectors to circumscribe a regular tetra decagon. Here, the regular tetra decagon circumscribes a circle having a diameter of 200 to 230 mm. The blank area is sandwiched by the axilla such that the C-shape detector unit 1 is positioned close to the surrounding of the breast m. Here, it is assumed that a direction from the root to the nipple of the breast m is a z-axis direction (see FIG. 4). A plurality of C-shape detector units 1 may be arranged in the z-axis direction.

Here, the γ-ray detector is a DOI (Depth of Interaction) detector having various scintillator blocks (not shown) laminated in a depth direction of γ-rays (e.g., laminated by four layers). Specifically, the DOI detector is formed by various scintillator blocks laminated in the depth direction of γ-rays. The DOI detector determines coordinate information in the depth direction causing to interaction and a horizontal direction (parallel to an incident surface) by calculating the center of gravity. Consequently, the DOI detector allows discrimination of a light source position in the depth direction (DOI: Depth of Interaction) where the interaction occurs.

In addition, the PET apparatus according to this embodiment further includes a coincidence circuit 2, a controller 3, an input unit 4, an output unit 5, and a memory 6. In FIG. 1, the controller 3 performs image processing including estimation of the scatter components (i.e., a function of a GPU (Graphics Processing Unit)) and other collective control integratedly. Alternatively, the controller 3 may be designed to perform the function of the GPU and the function of the controller individually.

The controller 3 controls the elements collectively that constitute the PET apparatus of the embodiment. The controller 3 is, for example, formed by a central processing unit (CPU) and the like.

The input unit 4 transmits data and commands inputted by an operator to the controller 3. The input unit 4 is formed by a pointing device typified by a mouse, a keyboard, a joystick, a trackball, and a touch panel. The output unit 5 is formed by a display unit typified by a monitor and a printer.

The memory 6 is composed of a storage medium typified by a ROM (Read-only Memory) and a RAM (Random-Access Memory). In the embodiment, the memory 6 writes and stores data into the RAM. The data is about coincidence such as a count value (count) coincidently counted by the coincidence circuit 2 and about various types of data arithmetically processed by the controller 3. Then the memory 6 reads the data from the RAM as appropriate. The memory 6 stores a program for performing various types of image processing (estimation of the scatter components in the embodiment) in advance in the ROM. The controller 3 executes the program to perform image processing depending on the program. In particular, programs on estimating scatter components are stored in the ROM. The programs contains reconstruction processing, projection processing (illustrated by a "Forward Projection" in FIG. 3), slice expanding processing, scatter component extraction (illustrated by "Deconvolution" in FIG. 3), and scatter scaling, which are to be mentioned later. The controller 3 executes the program on the scatter component extraction, thereby performing processes of steps S1 to S5 (see FIG. 3) mentioned later.

The scintillator block of the γ-ray detector converts γ-rays from the subject M with radiopharmaceutical administered thereto into light, and then a photomultiplier (PMT: Photo Multiplier Tube) of the γ-ray detector (not shown) multiplies and converts the light into electric signals. The electric signals are transmitted to the coincidence circuit 2 as events.

Specifically, when radiopharmaceutical is administered to the subject M, positrons of positron-emission type RI annihilate to generate two beams of γ-rays. The coincidence circuit 2 checks a position of the scintillator block and an incidence timing of the γ-rays. The coincidence circuit 2 determines the transmitted event as proper data only when the γ-rays enter coincidently into two scintillator blocks across the subject M. On the other hand, the coincidence circuit 2 rejects the data when the γ-rays enter into only one scintillator block. In other words, the coincidence circuit 2 detects coincident observation of γ-rays in two γ-ray detectors in accordance with the electric signals mentioned above.

The controller 3 receives the event from the coincidence circuit 2. The controller 3 performs image processing such as scatter component estimation or scattering correction, thereby obtaining a reconstruction image of the breast m of the subject M after the scattering correction. The controller 3 transmits the reconstruction image to the output unit 5. In this manner, tomography is conducted based on the reconstruction image obtained by the controller 3. A concrete function of the controller 3 is to be mentioned later.

As illustrated in FIG. 10C, the C-shape detector unit 1 as illustrated in FIGS. 1 and 2 includes the γ-ray detectors a part of which has a blank area. Accordingly, some γ-rays pass through the blank area and thus fail to be detected. Consequently, the data obtained with the C-shape detector unit 1 partially contains is partially missing.

Figure 3:
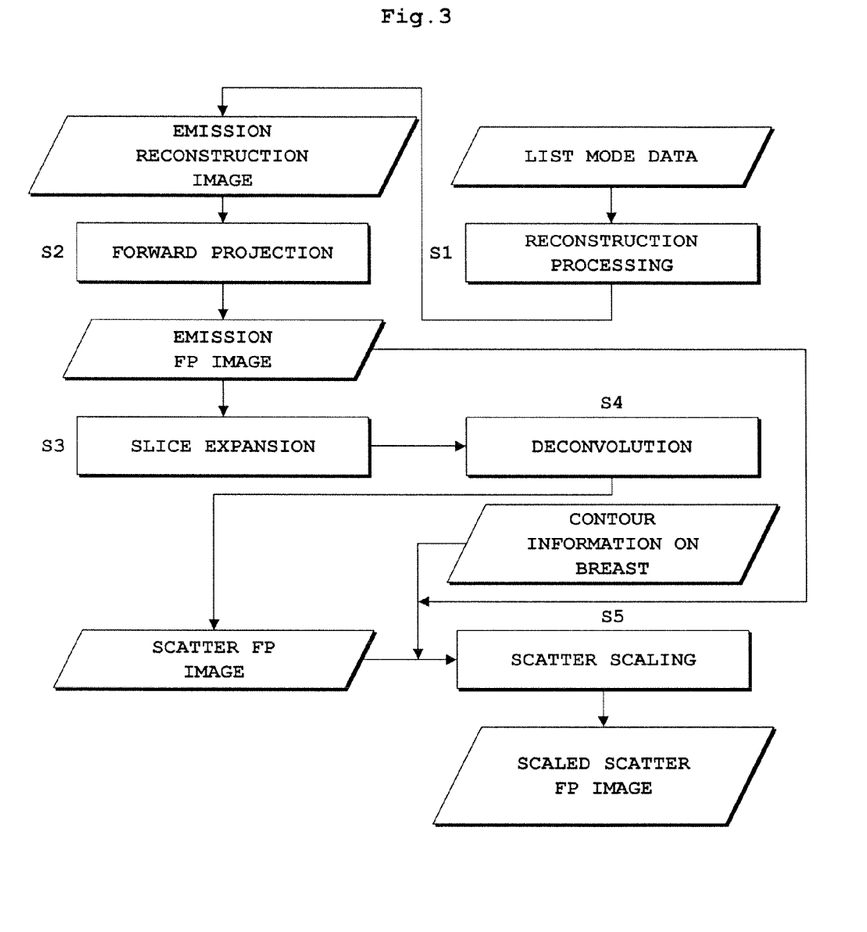
FIG. 3 is a flow chart illustrating a series of estimating scatter components written with each data.
Figure 4:
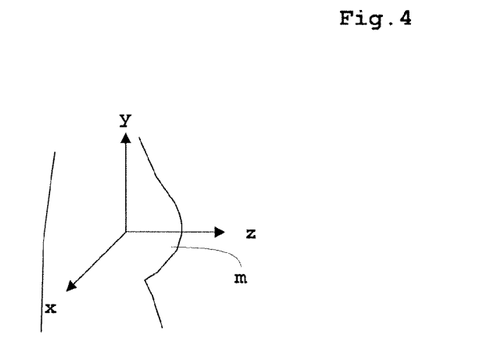
FIG. 4 is a schematic view of each axis of an orthogonal coordinate system about the breast.
Figure 5:
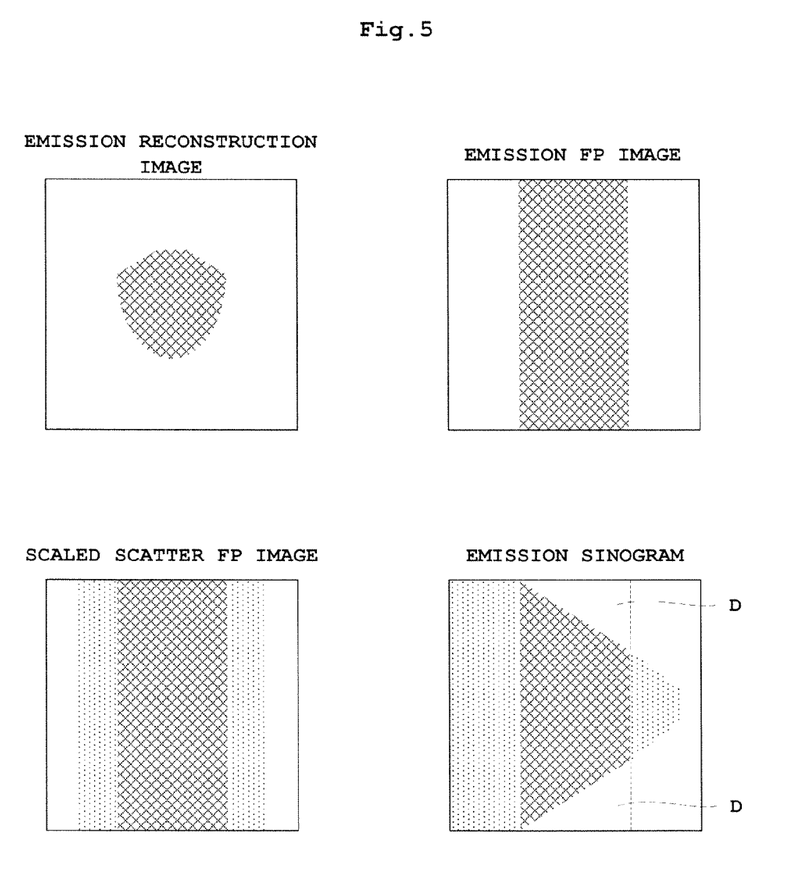
FIG. 5 is a schematic view of comparison between the conventionally sinogram and a projection image (FP image) according to the embodiment.
Figure 6A:
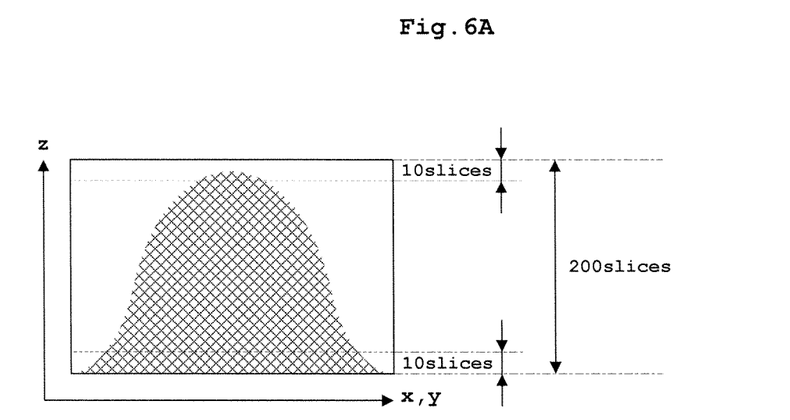
FIGS. 6A and 6B are schematic views each used for explanation of slice expansion.
Figure 6B:
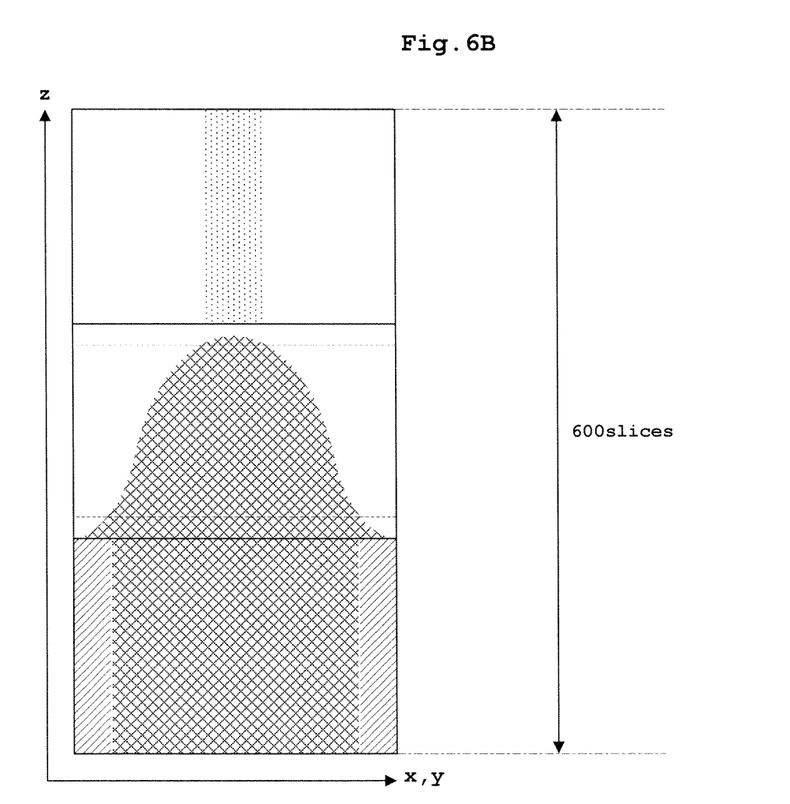

The following describes the concrete function of the controller 3 with reference to FIGS. 3-5, and FIGS. 6A and 6B. FIG. 3 is a flow chart illustrating a series of estimating the scatter components written with various types of data. FIG. 4 is a schematic view of each axis of the orthogonal coordinate system concerning the breast. FIG. 5 is a schematic view of comparison between the conventional sinogram and projection images (FP images) of the embodiment of the present invention. FIGS. 6A and 6B are schematic views each used for explaining slice expansion. Here, the controller 3 (see FIG. 1) executes the processes steps S1 to S5 in FIG. 3.

(Step S1) Reconstruction Processing

Firstly, as illustrated in FIG. 4, each axis of the orthogonal coordinate system is defined that concerns the breast m (see also FIG. 1). That is, a direction from the root to a nipple of the breast m is defined as a z-direction, a horizontal axis orthogonal to the z-axis as an x-direction, and a vertical axis orthogonal to the z-axis as a y-axis. The PET apparatus (mammography PET apparatus) with the C-shape detector unit 1 illustrated in FIGS. 1 and 2 performs radiography to the breast m (see FIGS. 1 and 4) of the subject M (see FIG. 1). The γ-ray detectors of the detector unit 1 transmit event data with positions of scintillator blocks and incidence timings of γ-rays to the coincidence circuit 2 (see FIG. 1) only upon detecting the γ-rays coincidently. The coincidence circuit 2 stores detection event information of the γ-rays in time sequence. The detection event information includes a number of detectors, a detection time, and energy of γ-rays. Consequently, list mode data is obtainable generated from the event data through detecting the γ-rays.

Then, reconstruction processing is performed to the list mode data to capture a reconstruction image. As the reconstruction processing, an iterative approximation method is adopted by which the image is that approximated and updated iteratively with use of the list mode data. The embodiment is described while applying a list-mode 3D DRAMA method (Dynamic Row-Action Maximum Likelihood Algorithm).

The following describes the list-mode DRAMA method in detail. Firstly, an LOR (Line of Response) is defined. Here, the LOR is a virtual line connecting two γ-ray detectors performing coincident counting. It is assumed that the i-th LOR is $L_i$ (i=0, 1, ..., I−1), the j-th pixel is $v_j$ (j=0, 1, ..., J−1), the total number of events detected with the γ-ray detectors is T, and an LOR corresponding to the t-th event (t=0, 1, ..., T−1) is i(t). Each of the events is divided by the number L of subsets $S_l$ (l=0, 1, ..., L−1). Moreover, it is assumed that pixel values of the pixels $v_j$ (j=0, 1, ..., J−1) immediately before and after updating the pixel values corresponding to the l-th subset in the k-th repeat are $x_j^{(k,l)}$, $x_j^{(k,l+1)}$ respectively.

An update expression of the pixel value $x_j^{(k,l)}$ can be given by the following Equation (1) without regarding an accidental event, a scatter event, and an effect of absorption.

Equation (1)

$$x_j^{(k,l+1)} = x_j^{(k,l)}\left\{1 + \frac{\lambda^{(k,l)}}{C_j} \cdot \sum_{i \in S_l} a_{i(t)j} \cdot \left(\frac{1}{\sum_{j'=0}^{J-1} a_{i(t)j'} x_{j'}^{(k,l)}} - p_{lj}\right)\right\}, \quad (1)$$

$$\lambda^{(k,l)} = \beta_0 / (\beta_0 + l + \gamma kl),$$

$$C_j = \max \sum_{i \in S_l} a_{i(t)j} p_{lj},$$

$$x_j^{(k+1,0)} = x_j^{(k,L-1)}$$

In the Equation (1), $a_{ij}$ denotes a detection probability, $\lambda^{(k,l)}$ denotes a relaxation parameter, and $C_j$ denotes a normalization matrix. The probability of $a_{ij}$ is a parameter with which the γ-rays generated from a pixel $v_j$ is detected in the i-th LOR ($L_i$). Here, the probability is known. In addition, $p_{lj}$ is referred to as a "Blocking Factor", and is selected optionally. In this embodiment, a Blocking Factor A is adopted with $p_{lj}$ independent of the value l (see the following Equation (2)).

Equation (2)

$$p_{lj} = \sum_{i=0}^{I-1} a_{ij} / L \quad (2)$$

Firstly, values $a_{ij}$ for all the conceivable numbers of LOR's (around $N_C^2/2$) are added for determining $\Sigma a_{ij}$ (i.e., the sum of $a_{ij}$ where j=0, 1, ...). Here, $\Sigma a_{ij}$ is an image having the same size as the reconstruction image, and expresses a probability of detecting the pixel $v_j$ in any LOR. Accordingly, $\Sigma a_{ij}$ is referred to as a "sensitivity distribution map". Using the sensitivity distribution map achieves determination of $C_j$ and $p_{ij}$ in the above Equation (1).

Specifically, $x_j^{(0,0)}$ as an initial image is set as appropriate. An image having a uniform pixel value may be adopted as the initial image $x_j^{(0,0)}$. Here, the number of $x_j^{(0,0)}$ is more than 0. The set initial image and a detection probability $a_{ij}$ (in the above Equation (1), $a_{i(t)j}$ with i→i(t)) are repeatedly substituted into the above Equation (1). Accordingly, $x_j^{(0,0)}, ..., x_j^{(0,L-1)}$ are iteratively determined. Then $x_j^{(0,L-1)}$ finally obtained is replaced by $x_j^{(1, 0)}$. Consequently, the image is moved up to an image $x_j^{(1, 0)}$. Likewise, $x_j$ is moved up ($x_j^{(0, 0)}, x_j^{(1, 0)}, \ldots, x_j^{(k, 0)}$. Here, the number k expressing frequency of repeat (update) is not particularly limited, but may be set as appropriate. Then $x_j$ finally determined as above is arranged for every pixel $v_j$ corresponding thereto. Consequently, the controller 3 performs reconstruction processing to the list mode data to obtain the reconstruction image.

The reconstruction image (illustrated as an "Emission reconstruction image" in FIGS. 3 and 5) is like the schematic view on the upper left of FIG. 5. FIG. 5 schematically illustrates other images with hatching for convenience. The step S1 corresponds to the reconstruction processing step in the present invention.

(Step S2) Forward Projection

The controller 3 projects the reconstruction image (Emission reconstruction image) in the step S1 to obtain a projection image. The projection image (illustrated as the "Emission FP image" in FIGS. 3 and 5) obtained through the projection processing (FP: Forward Projection) is like the schematic view on the upper right of FIG. 5. Various projection images including a projection image of the estimated scatter components and a projection image of the scaled scatter components are used as sinograms mentioned later. The step S2 corresponds to the projecting step in the present invention.

(Step S3) Slice Expansion

The controller 3 expands a slice by increasing the number of slices of the projection image (Emission FP image) in the step S2 under the assumption of radioactivity distribution of the trunk out of the field of view of the γ-ray detectors. As illustrated in FIGS. 6A and 6B, images of an average pixel value for ten slices on both ends in the z-axis direction are added to the upper and lower of the original projection image (Emission FP image). The number of slices to be added is equal to that of the original projection image (Emission FP image). The number of slices after the slice expansion is three times the number of the original projection image (Emission FP image).

Here, the slice is a cross section, and parallel to an xy-plane orthogonal to the z-axis. In FIGS. 6A and 6B, the longitudinal axis corresponds to the z-axis. When the photographing object is the breast m, the upper end of the drawings indicates a portion around the nipple, and the lower end indicates a portion around the root of the breast close to the trunk. As illustrated in FIG. 6A, the original projection image (Emission FP image) has 200 slices (illustrated as "200 slices" in FIG. 6A). Accordingly, the image having an average pixel value of 10 slices at the upper end (illustrated as "10 slices" in FIG. 6A) is added uniformly to the upper original projection image (Emission FP image) over 200 slices. Similarly, the image having an average pixel value of 10 slices at the lower end (illustrated by "10 slices" in FIG. 6A) is added uniformly to the lower original projection image (Emission FP image) over 200 slices. In this manner, when the original projection image (Emission FP image) has the 200 slices in FIGS. 6A and 6B, the number of slices after the slice expansion becomes 600 slices (illustrated "600 slices" in FIG. 6B), which is three times the number of slices of the original projection image (Emission FP image). The step S3 corresponds to the slice expanding step in the present invention.

(Step S4) Deconvolution

The projection image expanded through the step S3 is regarded as a sinogram. Here, a longitudinal axis of the sinogram is an angle direction, a horizontal axis of the sinogram is an x-axis direction (i.e., an x-coordinate in arrangement of the γ-ray detectors) as one axis of the orthogonal coordinate system. The two-dimensional sinogram is subjected to a two-dimensional Fourier transform to apply a low-pass filter to a spatial frequency distribution after the two-dimensional Fourier transform using a Deconvolution method. Consequently, an image with spatial frequency distribution having scatter components of radiation as low-frequency components is obtainable. Then, the image with the spatial frequency distribution of the scatter components is subjected to two-dimensional inverse Fourier transform to return it to an image in real space, whereby a projection image of the scatter components (illustrated as a "scatter FP image" in FIG. 3) is obtainable. In this manner, the low-frequency components are extracted from the projection image (Emission FP image) to obtain the scatter components. The step S4 corresponds to the scatter component extracting step in the present invention.

(Step S5) Scatter Scaling

For operation of the apparatus, the parameters determining the shape of low-pass filter are not optimized for every emission data. Accordingly, an error in distribution occurs between the projection image of the estimated scatter components (scatter FP image) and the projection image of the emission data (Emission FP image). In order to reduce the error, the projection image of the estimated scatter components (scatter FP image) is scaled so as to conform to the projection image of the emission data (Emission FP image) obtained in the step S2 in the lateral distribution (tail) of the subject M. In this case, scaling can be performed using contour information of the subject M.

Here, the lateral distribution of the contour information of the subject M (the breast m in the embodiment) is regarded as the scatter component. Then, each lateral distribution of the projection image of the scatter components (scatter FP image) and the projection image of the emission data (Emission FP image) is extracted from the contour information of the breast m, whereby a one-dimensional addition profile in a uniaxial direction to which the count values of γ-rays are added is determined in the angle direction of the sinogram. The uniaxial direction is the x-axis direction. When the subject M is out of the center of the field of view, the distribution is serpentine on the sinogram. Consequently, the foregoing serpentine sinogram is not suitable for determining the one-dimensional addition profile by adding all pieces of data divided in the angle direction (in this embodiment, divided into 128 pieces in the angle direction). Accordingly, the one-dimensional addition profile is determined by adding every eight pieces of data to totally obtain 16 segments of one-dimensional addition profiles (i.e., eight pieces/segment×16 segments=128 pieces). Next, a ratio in the one-dimensional addition profile of the projection image of the emission data (Emission FP image) to the projection image of the scatter component (scatter FP image) is determined. The average value of the ratios is used as a scaling coefficient of the slice. The projection image of the estimated scatter components (scatter FP image) is multiplied by the scaling coefficient. Assuming that the scaling coefficient is f, the scaling coefficient f is expressed for every slice using the following Equation (3) for calculation.

Equation (3)

$$f = \frac{1}{N} \sum_{x \in tail}^{N} \frac{E(x)}{S(x)} \qquad (3)$$

In the Equation (3), N denotes the number of pieces of data (the number of pixels) on the lateral distribution of contour image of the subject M (tail), E(x) denotes a one-dimensional addition profile in the x-direction of the projection image of the emission data (Emission FP image), S(x) denotes a one-dimensional addition profile in the x-direction of the scatter components of the projection image (scatter FP image). Accordingly, the ratio can be determined only with the lateral distribution of the contour information of the subject M. When the scaling coefficient is determined from a ratio on a medial distribution of the contour information of the subject M, the scaled projection image of the scatter components is overestimated.

The scaled projection image of the scatter components (illustrated as a "Scaled scatter FP image" in FIGS. 3 and 5) is like the schematic view illustrated on the lower left of FIG. 5. The step S5 corresponds to the scatter component scaling step in the present invention.

As mentioned above, the controller 3 executes the step S1 to S5. The projection image of the emission data (Emission FP image) is subjected to scattering correction using the scaled projection image of the scatter components (Scaled scatter FP image) obtained by the controller 3. Here, the scattering correction is well-known, and thus the description thereof is to be omitted. The controller 3 (see FIG. 1) transmits the reconstruction image of the breast m of the subject M after the scattering correction to the output unit 5 (see FIG. 1). At this time, the memory 6 (see FIG. 1) may store via the controller 3 the reconstruction image of the breast m of the subject M after the scattering correction. The image may be read out from the memory 6 as appropriate.

FIG. 5 schematically illustrates on the lower right thereof the sinogram of the data (illustrated as an "Emission sinogram" in FIG. 5) outputted by the apparatus including a conventional blank area. As is apparent from FIG. 5, the sinogram (Emission sinogram) illustrated on the lower right of the drawing contains a missing region D due to the γ-ray detectors. The regions extend from the upper left to the center of the right and from the center of the right to the lower left. In contrast to this, the projection image (Emission FP image) illustrated on the upper right of FIG. 5 and the scaled projection image of the scatter components (Scaled scatter FP image) illustrated in the lower left of the FIG. 5 each have a missing region where data is interpolated by the reconstruction processing in the step S1.

Result of Cylindrical Phantom

Figure 7:
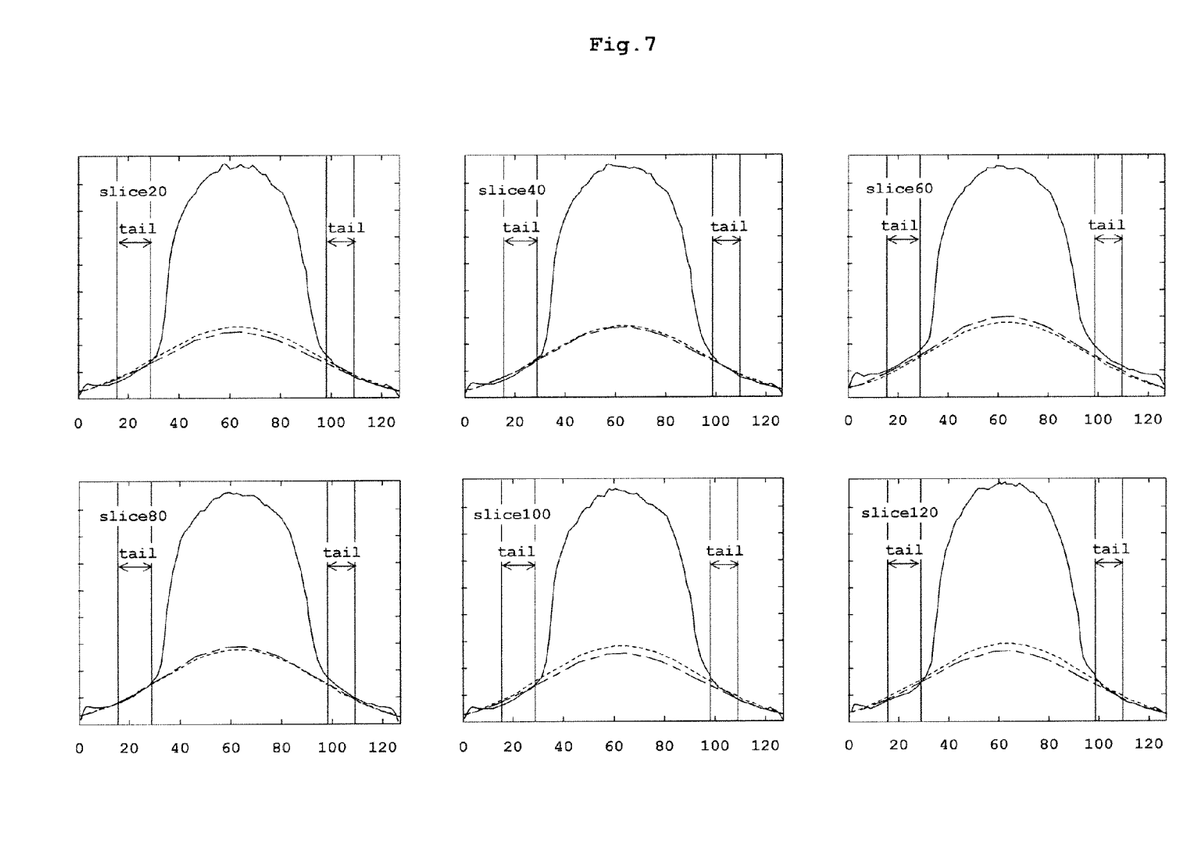
FIG. 7 is a result of estimating the scatter components using a cylindrical phantom according to the embodiment.

FIG. 7 illustrates the result of a cylindrical phantom estimating scatter components with the present invention. Each graph is a one-dimensional addition profile in the angle direction of one slice. It can be confirmed from FIG. 7 that the distribution of the emission data conforms to that of scaled scattering in each slice at tails on the lateral cylindrical phantom. Here, FIG. 7 illustrates the one-dimensional addition profile of the emission data with solid lines, the one-dimensional addition profile of scatter before scaling with dotted lines, and the one-dimensional addition profile of scatter after scaling with dashed-dotted lines.

Result of Scattering Correction

Figure 8:
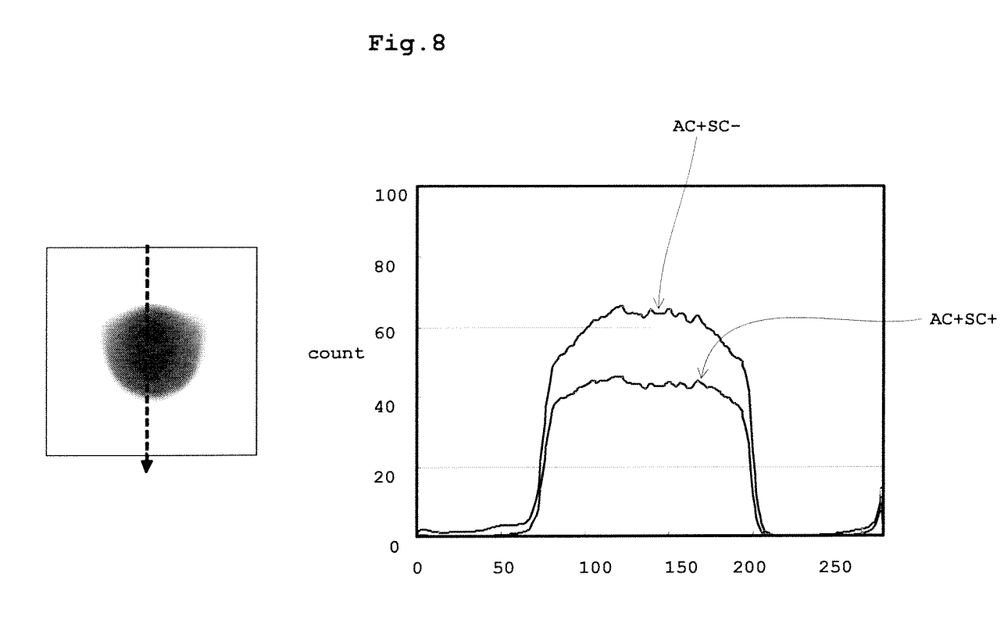
FIG. 8 is a result of scattering correction by a list-mode 3D DRAMA method using the estimated scatter components.

FIG. 8 illustrates the result of the scattering correction by the list-mode 3D DRAMA method with use of the estimated scatter components according to the present invention. FIG. 8 illustrates on the left thereof an average image of the reconstruction image, whereas illustrates on the right thereof distribution in a vertical direction (dotted lines) of the average image. FIG. 8 makes comparison between no scattering correction (illustrated as "AC+SC−" in the drawing) and scattering correction (illustrated as "AC+SC+" in the drawing). Here, "AC" denotes absorption correction (absorptive correction). Accordingly, absorption correction is performed regardless of scattering correction. It can be confirmed from FIG. 8 that the data is a cylindrical phantom and includes uniform adioactivity distribution. Moreover, it can be confirmed that the scattering correction causes elimination of the scatter components outside the phantom, thereby generating uniform distribution within the phantom.

The scatter component estimating method concerning the steps S1 to S5 in FIG. 3 differs from the conventional method of obtaining a reconstruction image finally by performing reconstruction processing to histogram or list mode data and a method of directly estimating scatter components from sinograms as described in Non-Patent Literature 1. That is, in the reconstruction processing S1, the reconstruction processing is performed to the event data (list mode data in the embodiment) to firstly capture a reconstruction image. Then, in the Forward Projection (the projection processing step) in step S2, the reconstruction image obtained in the reconstruction processing step S1 is projected to capture a projection image (Emission FP image). Then, in the Deconvolution step (scatter component extracting step) S4, low-frequency components are extracted from the projection image obtained in the Forward Projection (projection processing step) S2 to obtain scatter components. In the embodiment, the projection image is further expanded through the slice expansion step S3. As noted above, the reconstruction image obtained from the event data (list mode data) is not used as final data. The low-frequency components are extracted from the projection image (Emission FP image) to obtain the scatter components. The projection image is obtainable from the event data (list mode data) via the reconstruction image. That is, for applying the method of Non-Patent Literature 1 to the sinogram having data with a missing region, the missing region has to be eliminated. As noted above, even when the data contains the missing region, the reconstruction processing unlikely to be influenced by the missing region suppresses the influence by the missing region, and the resultant reconstruction image is projected. Consequently, the projection image (Emission FP image) having dummy data being interpolated to the missing region is obtainable. See FIG. 5. As a result, projection from the event data (list mode data) through the reconstruction image achieves the projection image (Emission FP image) with a suppressed influence by the data missing. Accordingly, precious estimation of the scatter components is obtainable by extracting the low-frequency components from the projection image (Emission FP image).

It is preferable in the embodiment to perform scaling of the scatter components through the scatter scaling step S5, the scatter components being obtained with the Deconvolution method (scatter component extracting step) S4 using the projection image (Emission FP image obtained from the list mode data in the embodiment) and contour information of the subject M (contour information of the breast m in FIG. 3). As described in the step S5, an error in distribution occurs between the projection image of the estimated scatter components (scatter FP image) and the projection image of the emission data (Emission FP image). In order to reduce the error, the projection image of the estimated scatter components (scatter FP image) is scaled such that the distribution thereof conforms to the distribution of the projection image of the emission data (Emission FP image) obtained in the step S2. In this case, scaling can be performed using the contour information of the subject M.

The contour information of the subject M may be form information such as the transmission data mentioned above, or CT data obtained with an X-ray CT apparatus. Alternatively, the form information may be obtained from the projection image of the emission data through contour extraction. Assuming that the projection image (Emission FP image obtained from the list mode data in the embodiment) is the sinogram having the angle direction and the uniaxial direction (the x-direction in the embodiment) of the orthogonal coordinate system, a one-dimensional addition profile in the uniaxial direction (the x-direction) is determined with count values of the radiation being added in the angle direction of the sinogram. Then, a ratio $(E(x)/S(x))$ in the one-dimensional addition profile of the projection image (Emission FP image) to the scatter components (scatter FP image) obtained with the Deconvolution step S4 (the scatter component extracting step) is determined from the contour information of the subject M mentioned above in the lateral distribution of the contour information of the subject M. Thereafter, a scaling coefficient f is determined in accordance with the ratio $(E(x)/S(x))$ in the one-dimensional addition profile for use in scaling of the scatter components.

In the embodiment, the reconstruction processing in the reconstruction processing step S1 is an iterative approximation method by which an image is iteratively approximated with the event data (list mode data in the embodiment). Here, the list-mode 3D DRAMA method is adopted, but is not limited for the iterative approximation method. For instance, such as an ML-EM (Maximum Likelihood Expectation Maximization) method, a static RAMLA (Row-Action Maximum Likelihood Algorithm) method, or an OSEM (Ordered Subset ML-EM) method may be adopted as long as it is the iterative approximation method by which an image is iteratively approximated with the event data (list mode data).

The scatter component estimating method according to the embodiment of the present invention is especially advantageous for use of the data as missing data. That is, the mammography PET apparatus as in FIG. 1 includes a C-shape detector unit 1 a part of which is open. The scatter component estimating method according to the embodiment of the present invention is advantageous for estimating the scatter components of radiation (γ-rays) using the data with the missing region from the event data (the list mode data in the embodiment). The data with the missing region is obtained with the detector unit 1 and is thus partially missing. As mentioned above, the reconstruction unlikely to be influenced from the missing is performed to reduce an influence of the missing. Accordingly, dummy data is interpolated to the missing region of the projection image (Emission FP image) obtained by projecting the reconstruction image. See FIG. 5. Then, the resultant is used as the projection image (Emission FP image) with a suppressed influence of the missing data. Consequently, precious estimation of the scatter components is obtainable by extracting the low-frequency components from the projection image (Emission FP image).

In the embodiment, the slice of the projection image (Emission FP image) obtained from the event data (list mode data in the embodiment) is expanded in the slice expanding step S3. The low-frequency components are extracted from the projection image (Emission FP image) expanded in the slice expanding step S3 to obtain the scatter components the Deconvolution (scatter component extracting step) S4. Such is preferable. When radioactivity distribution exists outside the field of view, the slice is expanded by increasing the number of slices of the projection image under the assumption of the radioactivity distribution. When the slice of the projection image (Emission FP image) fails to be expanded with the radioactivity distribution, the scatter components are underestimated at the end of the image (e.g., in the vicinity of the root of the breast m close to the trunk when a photographing object is the breast m). Thereafter, the scatter components are scaled to be extremely overestimated in the following scaling (step S5). The slice of the projection image (Emission FP image) is expanded when the radioactivity distribution exists outside the field of view, leading to elimination of the underestimation of the scatter components at the end. Accordingly, overestimating the scatter components can be prevented without the following extreme scaling of the scatter components.

The present invention is not limited to the foregoing embodiment, but may be modified as under.

1. In the embodiment mentioned above, the mammography PET apparatus has been described as one example of an emission tomography apparatus. Alternatively, the embodiment is applicable to an apparatus in combination of a PET apparatus and another modality apparatus (e.g., an X-ray CT apparatus).

2. In the embodiment mentioned above, the mammography PET apparatus that performs photography of the breast of the subject has been described. However, the photographing object is not limited to the breast. Specifically, the embodiment is applicable to a PET apparatus for head that captures a reconstruction image of the head of the subject. Alternatively, the embodiment is also applicable to a PET apparatus for the whole body that captures a reconstruction image of the whole body of the subject.

Figure 9:
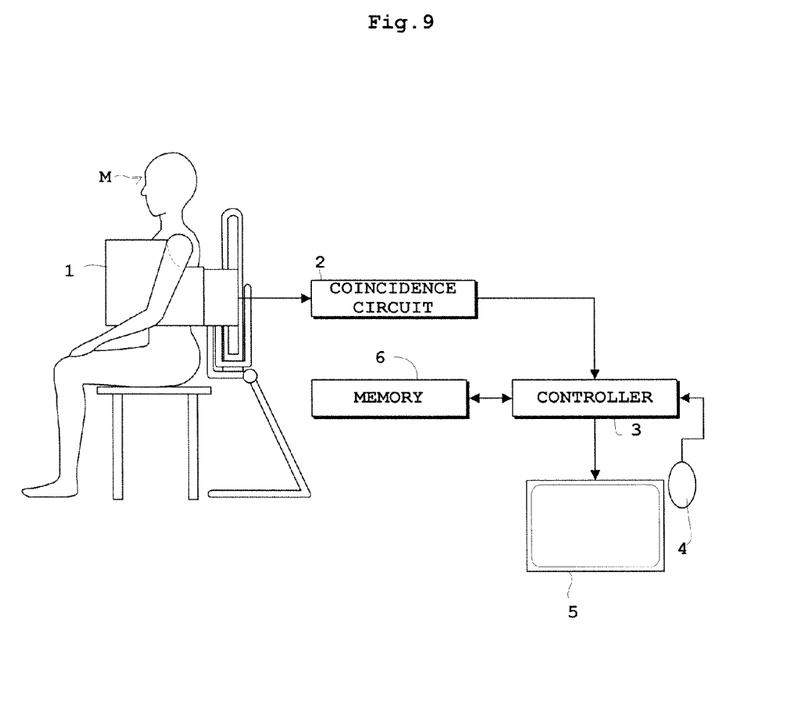
FIG. 9 is a side view and a block diagram of a PET apparatus according to one modification.

3. In the embodiment mentioned above, the C-shape detector unit 1 in FIGS. 1 and 2 has been described as one example of a detector unit a part of which is open. However, the C-shape detector unit 1 in FIGS. 1 and 2 is not limitative. A detector unit is applicable having a plurality of γ-ray detectors being arranged in parallel to face to each other. Besides, the mammography PET apparatus is applicable to a detector unit 1 as in FIG. 9 sandwiched by both sides of the subject. Here, a detection plate with the detector unit 1 embedded therein includes a notch. Both sides of the subject sandwich the notch with the axilla to perform photography of the breast. A plurality of γ-ray detectors is arranged one outside another within the detection plate along the notch.

4. In the embodiment mentioned above, the C-shape detector unit 1 in FIGS. 1 and 2 has been described as one example of the detector unit a part of which is open. Alternatively, the detector unit having a partial-ring shape other than the C-shape as in FIG. 10B may be adopted. Moreover, a detector unit may be adopted having a plurality of γ-ray detectors arranged in parallel so as to face to each other as mentioned above. Moreover, it is not always necessary to use the detector unit a part of which is open. That is, a full-ring detector unit as in FIG. 10A may be adopted.

5. In the embodiment mentioned above, the scatter components of radiation (γ-rays) are estimated using the missing-region data from the event data (list mode data in the embodiment). The missing region data partially contains the missing region due to the detector unit, such as the C-shape detector unit 1 in FIGS. 1 and 2. Here, a part of the detector unit is open. However, it is not always necessary to estimate the scatter components of radiation (γ-rays) using the missing-region data from the event data (list mode data). That is, the embodiment is applicable to the data obtained from the full-ring detector unit in FIG. 10A mentioned above.

6. Moreover, the embodiment is applicable to a PET apparatus having a detector unit supported on a movable cart for installation in the vicinity of another modality apparatus (e.g., an X-ray CT apparatus).

7. In the embodiment mentioned above, the γ-ray detector is a DOI detector having various scintillator blocks laminated in the depth direction of γ-rays. Alternatively, a detector having one layer of various scintillator blocks may be adopted.

Figure 11:
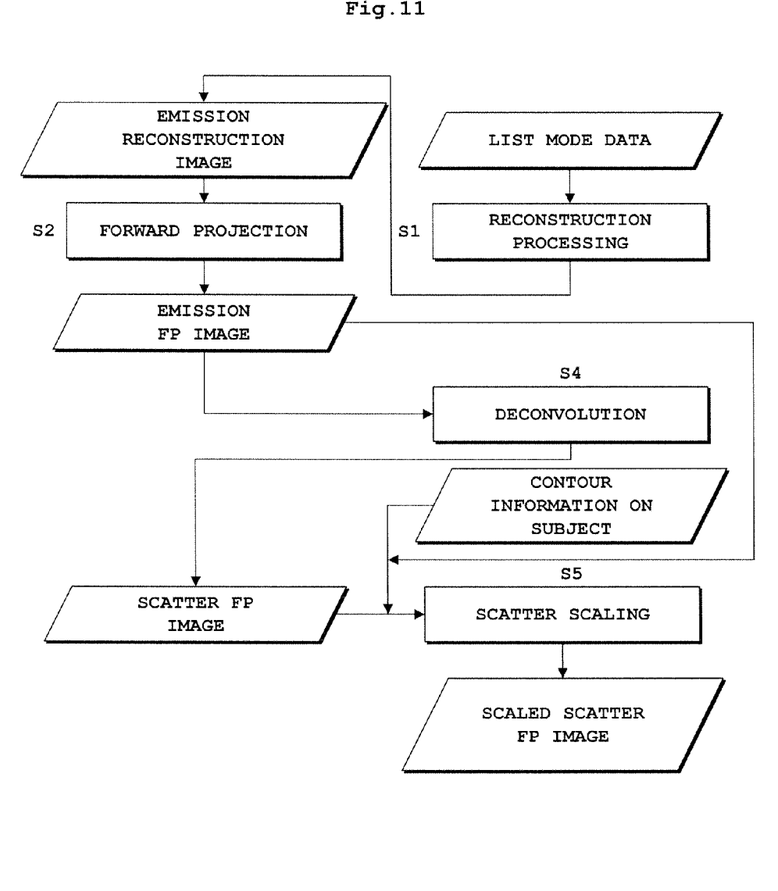
FIG. 11 is a flow chart illustrating a series of estimating scatter components written with each data according to the modification.

8. In the embodiment mentioned above, the PET apparatus for a human body as the subject has been described. Alternatively, the embodiment is applicable to a PET apparatus for small animals for performing radiography of a small animal (e.g., a mouse). Here, when no large radioactivity distribution exists out of the field of view such as for the PET apparatus for small animals, there is no need to assume the outside of the field of view. Accordingly, the slice expanding step mentioned above is not required. In FIG. 11, the slice expansion step S3 of FIG. 3 is not shown. In the embodiment of FIG. 3, the contour information of the subject is limited to that of the breast. In FIG. 11, the contour information of the subject is other than that of the breast since a target in the drawing is other than the breast (e.g., small animals).

9. In the embodiment mentioned above, the slice is expanded by increasing the number of slices for a portion in the vicinity of the root (lower end) of the breast close to the trunk as illustrated in FIGS. 6A and 6B. However, this is not limitative. Specifically, taking into consideration that the scatter components are likely to be underestimated at a portion in the vicinity of the root of the breast close to the trunk rather than a portion close to the nipple, only the root (lower end) of the breast close to the trunk may be expanded by increasing the number of slices at the lower end.

10. The embodiment mentioned above performs the scatter component scaling step. However, the scatter component scaling step may be omitted when the error in distribution between the projection image of the estimated scatter components and the projection image of the emission data is out of consideration. Examples of the above case include a phantom experiment with no radioactivity distribution outside the field of view.

11. In the embodiment mentioned above, the contour information of the subject is not particularly limited as long as it contains some contour information. For instance, the contour information of the subject may be form information such as transmission data and CT data obtained with the X-ray CT apparatus, or form information obtained from the projection image of the emission data through the contour extracting mentioned above.

12. In the embodiment mentioned above, the controller 3 is constituted by a device for performing image processing including the scatter component estimation. However, the device is not limited to the central processing unit (CPU). For instance, a device may perform image processing with a programmable device (e.g., an FPGA (Field Programmable Gate Array)) having a hardware circuit (e.g., logic circuit) inside thereof being variable depending on program data.

13. In the embodiment mentioned above, the reconstruction processing is performed to the list mode data. However, it is not limited to the list mode. The reconstruction processing may be performed to the sinogram (histogram) as long as the data is generated from the event data. Moreover, the iterative approximation method may be adopted by which an image is iteratively approximated and updated using the event data other than the list mode data (e.g., sinogram). Alternatively, the scatter components of radiation may be estimated from the event data. In addition, the slice of the projection image may be expanded that is obtained from the event data.

INDUSTRIAL APPLICABILITY

As noted above, the present invention is suitable for a radiation tomography apparatus with a detector unit, such as a partial-ring detector unit including a C-shape detector unit, a part of which is open.

The present invention may be embodied in other specific forms without departing from the spirit or essential attributes thereof and, accordingly, reference should be made to the appended claims, rather than to the foregoing specification, as indicating the scope of the invention.

REFERENCE SIGNS LIST

1 . . . detector unit
3 . . . controller
$E(x)$ . . . one-dimensional addition profile in x-direction of Emission FP image
$S(x)$ . . . one-dimensional addition profile in x-direction of scatter FP image
$E(x)/S(x)$ . . . ratio of one-dimensional addition profile
f . . . scaling coefficient
m . . . breast
M . . . subject

What is claimed is:

1. A scatter component estimating method for estimating scatter components of radiation from data collected in a radiation tomography apparatus, the method comprising:
   a reconstruction processing step of performing reconstruction processing to event data obtained by detecting the radiation to capture a reconstruction image;
   a projecting step of projecting the reconstruction image obtained in the reconstruction processing to capture a projection image, after the reconstruction processing step; and
   a scatter component extracting step of extracting low-frequency components from the projection image obtained in the projecting step to obtain scatter components, after the projecting step.

2. The scatter component estimating method according to claim 1, further comprising:
   a scatter component scaling step of performing scaling of the scatter components obtained in the scatter component extracting step using the projection image and contour information of a subject.

3. The scatter component estimating method according to claim 2, further comprising steps of:
   upon determination that the projection image is a sinogram composed of an angle direction and a uniaxial direction of an orthogonal coordinate system, determining a one-dimensional addition profile in the uniaxial direction with count values of the radiation being added in the angle direction of the sonogram;
   determining a ratio in one-dimensional addition profile of the projection image to the scatter components obtained in the scatter component extracting step from lateral distribution of the contour information of the subject; and
   determining a scaling coefficient in accordance with the ratio in the one-dimensional addition profile for using the scaling coefficient in scaling the scatter components.

4. The scatter component estimating method according to claim 1, wherein the reconstruction processing in the reconstruction processing step is an iterative approximation method by which an image is iteratively approximated with the event data.

5. The scatter component estimating method according to claim 1, wherein
the radiation tomography apparatus includes a detector unit having an open, part, and
the scatter components of the radiation are estimated using data with a missing region from the event data, the data with the missing region being obtained with the detector unit and partially missing.

6. The scatter component estimating method according to claim 1, further comprising:
a slice expanding step of expanding a slice of the projection image obtained from the event data, wherein
in the scatter component extracting step, the low-frequency components are extracted from the projection image having been expanded in the slice expanding step for obtaining the scatter components.

7. The scatter component estimating method according to claim 5, wherein
the detector unit has a partial-ring shape including an opening part, and
the scatter components of the radiation is estimated using the data with the missing region from the event data, the data with the missing region being obtained with the detector unit having the partial-ring shape.

8. The scatter component estimating method according to claim 7, wherein
the detector unit having the partial-ring shape is a C-shape detector unit.

9. The scatter component estimating method according to claim 5, wherein
the detector unit has a plurality of detectors arranged in parallel so as to face to each other, and
the scatter components of the radiation are estimated using the data with the missing region from the event data, the data with the missing region being obtained with the detector unit.

10. The scatter component estimating method according to claim 2, wherein
the contour information of the subject is transmission data obtained by externally emitting radiation of the same type as radiopharmaceutical, and
the scatter components are scaled using the projection image and the transmission data.

11. The scatter component estimating method according to claim 2, wherein
the contour information of the subject is CT data obtained with an X-ray CT apparatus, and
the scatter components are scaled using the projection image and the CT data.

12. The scatter component estimating method according to claim 2, wherein
the contour information of the subject is form information obtained from the projection image of emission data through contour extraction, the emission data generated from the subject with radiopharmaceutical administered thereto, and
the scatter components are scaled using the projection image and the form information.

* * * * *